United States Patent [19]

Tomaja

[11] 4,186,175

[45] Jan. 29, 1980

[54] CROWN ETHER URANYL HALIDE COMPLEXES

[75] Inventor: David L. Tomaja, Bartlesville, Okla.

[73] Assignee: Phillips Petroleum Company, Bartlesville, Okla.

[21] Appl. No.: 872,144

[22] Filed: Jan. 25, 1978

[51] Int. Cl.$^2$ .................. B01J 1/10; C07D 323/00; C01G 43/02

[52] U.S. Cl. .................. 204/158 R; 260/338; 260/340.3; 423/10; 423/261

[58] Field of Search .............. 260/338, 340.3; 423/10, 423/261; 252/301.1 R; 204/157.1 R, 158 R

[56] References Cited

U.S. PATENT DOCUMENTS

| | | | |
|---|---|---|---|
| 2,758,007 | 8/1956 | Ballard | 423/10 |
| 3,562,295 | 2/1971 | Pedersen | 260/338 |
| 3,622,577 | 11/1971 | Pedersen | 260/338 X |
| 3,687,978 | 8/1972 | Pedersen | 260/338 X |
| 3,814,700 | 6/1974 | Aviram et al. | 252/408 |
| 3,873,569 | 3/1975 | Pedersen | 260/340.3 |
| 3,914,373 | 10/1975 | Jepson | 260/340.3 X |
| 3,923,619 | 12/1975 | DePoorter et al. | 423/253 X |
| 3,987,061 | 10/1976 | Pedersen | 260/340.3 X |
| 3,997,565 | 12/1976 | Kauer | 260/340.3 |
| 4,024,158 | 5/1977 | Kauer | 260/340.3 |

OTHER PUBLICATIONS

Pedersen, C. J., "Crystalline Salt Complexes of Macrocyclic Polyethers", in *J.A.C.S.* 92(2): 386–391 (1970).
Seminara, A. et al., "Uranyl Complexes with Cyclic Polyethers", in *Inorg. Chim. Acta* 20: 105–108 (1976).
Eller, P. G., et al., *Inorg. Chem.* 15(10): 2439–2442 (1976).
Tomaja, D. L., "Uranyl Complexes of Some Crown Ethers", in *Inorg. Chim. Acta* 21(2): L31–32.
Pederson, C. J. et al., "Macrocyclic Polyethers and their Complexes", in Angew. Chem. Internat. Edit 2(1): 16–25 (1972).
Truter et al., "Cryptates".
Pedersen, C. J., "Ionic Complexes of Macrocyclic Polyethers", in *Federation Proceedings*, 27(6): 1305–1309 (1968).
Costes, R. M. et al., *Inorg. Nucl. Chem. Letters* 16(7–8): 469–473 (1975).
Coste, R. M. et al., Inorg. Nucl. Chem. Letters 12(1): 13–21 (1976).
Chem. & Eng. News, 55(23): 21 (Jun. 6, 1977).
Rainowitch, E. et al., *Spectroscopy and Photochemistr. of Uranyl Compounds*, Perganon Press, N.Y. 1964, pp. 257–263; 350–352.

*Primary Examiner*—Richard E. Schafer

[57] ABSTRACT

Uranium oxide is recovered from an aqueous solution of uranyl halides by extracting uranyl halide from the aqueous solution with an organic liquid, forming a crown ether uranyl halide complex in the organic liquid, and then contacting the uranyl halide crown ether complex with water, carboxylate ion, and light under suitable conditions. Also disclosed are certain novel crown ether uranyl halide complexes and their preparation. Also disclosed is the use of 18-crown-6 to selectively recover uranyl halide from a solution thereof containing other metal salts.

45 Claims, No Drawings

CROWN ETHER URANYL HALIDE COMPLEXES

This invention relates to a method for producing uranium oxide from uranyl halides. In another aspect this invention relates to a method for obtaining uranium oxide from aqueous solutions containing uranyl halides. In still another aspect, this invention relates to novel crown ether uranyl halide complexes that are useful in preparing triuranium octaoxide. In yet another aspect this invention relates to methods of preparing novel crown ether uranyl halide complexes. In still a further aspect, this invention relates to a process for selectively recovering uranyl halide from a solution thereof containing other metal salts.

Uranium oxides are well known and widely used in the industry as starting materials for a variety of uranium-containing compounds. The term "uranium oxide" as used herein is intended to refer generally to any of the compounds consisting of uranium and oxygen atoms. The term is also intended to refer to those compounds consisting of uranium and oxygen atoms which have water of hydration associated therewith. Generally, uranium oxides are obtained by treatment of uranium ores.

The present invention provides a method whereby uranium oxide can be readily produced from the uranyl halides contained in many commonly available aqueous solutions. Examples of aqueous solutions which often include significant amounts of uranyl halides include the tailings of uranium ore processing mills, the leach liquors of uranium ore processing mills, and the solvents used in uranium ore extraction processes. Also sea water and even some natural subsurface water contain some concentrations of uranyl halides.

An object of the present invention is to provide a method for obtaining uranium oxide from aqueous solutions of uranyl halide.

Another object of the present invention is to provide a method for converting uranyl halides to triuranium octaoxide.

Still another object of the present invention is the production of novel crown ether uranyl halide complexes that are useful as intermediates in the production of triuranium octaoxide.

Still another object of the present invention is to provide a method for selectively recovering uranyl halide from a solution thereof also containing at least one other metal halide selected from the group consisting of nickel halide or copper halide.

Other aspects, objects, and advantages of the instant invention will be apparent to those skilled in the art following a reading of the instant disclosure.

In accordance with one aspect of the instant invention, novel stable crown ether complexes which are readily converted to uranium oxide are produced by admixing in a suitable liquid a uranyl halide with a crown ether selected from the group consisting of dicyclohexano-18-crown-6 and crown ethers wherein the cyclic ring consists of 4 to 10 - O - J - units wherein J for a particular compound is

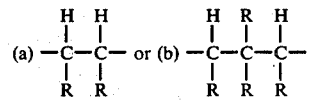

wherein each R is independently selected from the group consisting of hydrogen and alkyl radicals having from 1 to 4 carbon atoms, or wherein at least one J is (b) and the remaining J's are (a).

Preferably, when the crown ethers have alkyl substituents on the ring, the alkyl substituents will have only one or two carbon atoms. Further, the preferred crown ethers in the cyclic ring are formed of no more than 24 atoms. Typical examples of suitable crown ethers that can be employed in this invention include:

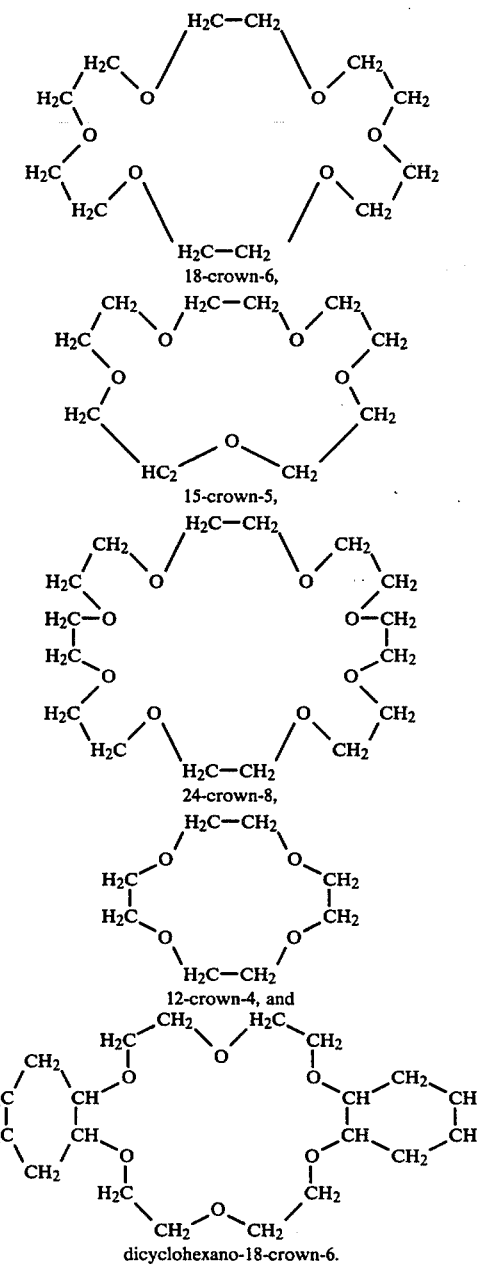

Liquids suitable as reaction diluents for the preparation of the novel crown ether complexes are any liquids which do not dissociate the crown ether complexes. Preferably, the reactants have at least a slight amount of solubility in the liquid. Examples of suitable liquids include methanol, ethanol, acetic acid, diethyl ether, and tetrahydrofuran. Water is not a suitable liquid as it causes the inventive crown ether complexes to dissociate. Accordingly, the liquid employed should not contain more than about 1 weight percent of water; preferably the liquid should contain no more than about 0.5 weight percent of water. An especially preferred liquid is anhydrous acetic acid. Also preferred is the liquid resulting when a sufficient amount of acetic anhydride is added to acetic acid to give an anhydrous liquid. When glacial acetic acid is employed, generally about 5 to about 10 weight percent of acetic anhydride based on the weight of the acetic acid is sufficient to obtain such an anhydrous liquid.

Generally any uranyl halide is considered suitable for forming a complex in accordance with this invention. Uranyl chloride, uranyl bromide, and uranyl iodides, or their hydrates, are especially preferred.

The temperature and pressure for the admixing are not considered critical. Any temperature and pressure can be employed which results in the reaction being carried out in a liquid. Preferably the temperature is in the range of about 20° C. to about 40° C. and the pressure is atmospheric.

While the complexes generally form almost instantaneously upon the admixing of the reactants, the admixing can be continued for any period of time which provides the desired amount of uranium complex.

The amount of liquid diluent used in admixing the uranyl halide and crown ether in accordance with this invention is not considered to be critical. Generally, the ratio of weight of the liquid diluent to the combined weights of the uranyl halide and crown ether is in the range of about 3:1 to about 20:1.

The uranyl halide and the crown ether can be combined in any molar ratio which results in a recoverable amount of uranyl halide crown ether complex. Generally the molar ratio of uranyl halide to crown ether for significant yields will be in the range of about 0.1:1 to about 10:1. Preferably the molar ratio of uranyl halide to crown ether is about 1:1.

The crown ether complexes produced can be recovered by any suitable technique known for recovering solids from a diluent. Preferably the crown ether complexes are precipitated from the liquid and recovered by filtration. Cooling can assist the precipitation. Also the addition of small amounts of liquids in which the complex is less soluble can also assist the precipitation. The recovered crown ether complexes can be purified by washing with a liquid which does not cause dissociation of the complex. Generally solvents for the complexes do cause dissociation.

In accordance with a preferred embodiment of the instant invention, stable anhydrous crown ether uranyl halide complexes are produced by admixing in a suitable anhydrous liquid, an anhydrous uranyl halide with a crown ether as defined above.

The following examples illustrate the present inventive methods of preparing uranyl halide crown ether complexes.

EXAMPLE I

To 1.79 gms (0.0045 mole) of uranyl chloride trihydrate, i.e., $UO_2Cl_2.3H_2O$, dissolved in 10 ml of glacial acetic acid was added 1.0 gm (0.0045 mole) of 15-crown-5 in 10 ml of acetic acid at ambient temperature. After stirring for 30 minutes, a light yellow precipitate was separated by filtration, washed with diethyl ether, and dried in vacuo to yield 2.1 gms of $UO_2Cl_2.(15\text{-crown-5}).3H_2O$.

EXAMPLE II

To about 0.5 gm (about 0.0013 mole) of uranyl chloride trihydrate dissolved in 30 ml of diethyl ether was added 1.0 gm (0.0045 mole) of 15-crown-5. A light yellow solid precipitated immediately. After stirring for 30 minutes at ambient temperature, the precipitate was recovered by filtration and dried in vacuo to yield 0.5 gm of $UO_2Cl_2.(15\text{-crown-5}).3H_2O$.

EXAMPLE III

To a solution of 0.9 gm (0.005 mole) of 12-crown-4 in 10 ml of acetic acid was added 1.98 gms (0.005 mole) of $UO_2Cl_2.3H_2O$ in 10 ml acetic acid. After 12 hours of stirring at ambient temperature, a light yellow solid was isolated by filtration, washed with diethyl ether, and dried in vacuo to yield 0.6 gm of $UO_2Cl_2.(12\text{-crown-4}).2H_2O$.

EXAMPLE IV

Under an anhydrous atmosphere, 1.0 gm (0.0038 mole) of 18-crown-6 dissolved in 10 ml of anhydrous acetic acid was admixed with 10 ml anhydrous acetic acid containing 1.29 gms (0.0038 mole) of $UO_2Cl_2$. After 30 minutes of stirring at ambient temperature, a light yellow solid was separated by filtration, washed with diethyl ether, and dried in vacuo to yield 1.4 gms of $(UO_2Cl_2)_2.(18\text{-crown-6})$.

EXAMPLE V

Under an anhydrous atmosphere, 1.0 gm (0.0045 mole) of 15-crown-5 in glacial acetic acid containing 5–10 weight percent acetic anhydride was added to 1.55 gms (0.0045 mole) of $UO_2Cl_2$ in an identical acetic acid solvent. After 30 minutes of stirring at ambient temperature, a light yellow solid was separatd by filtration, washed with diethyl ether, and dried in vacuo to yield 0.5 gm of $(UO_2Cl_2)_2.(15\text{-crown-5})_3.2HCl$.

EXAMPLE VI

Under an anhydrous atmosphere, 1.0 gm (0.0057 mole) of 12-crown-4 in 10 ml of glacial acetic acid containing 5–10 percent acetic anhydride was admixed with a solution of 1.94 gms (0.0057 mole) of uranyl chloride in 10 ml of acetic acid containing 5–10 weight percent acetic anhydride. After 30 minutes of stirring at ambient temperature, a solid was isolated by filtration, washed with diethyl ether, and dried in vacuo to yield 0.3 gm of $UO_2Cl_2.(12\text{-crown-4})$.

EXAMPLE VII

Under an anhydrous atmosphere, 1.0 gm (0.0027 mole) of dicyclohexano-18-crown-6 in 10 ml of acetic acid containing 5–10 percent acetic anhydride was added 0.92 gm (0.0027 mole) of $UO_2Cl_2$ in 10 ml of acetic acid containing 5–10 weight percent acetic anhydride. After 30 minutes of stirring at ambient temperature, a solid was isolated by filtration, washed with diethylether, and dried in vacuo to yield 0.6 gm of $(UO_2Cl_2)_2.(\text{dicyclohexano-18-crown-6})$.

The composition of the products of the above Examples is based on their elemental analysis and infrared spectra. The elemental analysis of the complexes gave the following results:

| Complex | Calculated, % | | | Found, % | | |
|---|---|---|---|---|---|---|
| | C | H | Cl | C | H | Cl |
| $UO_2Cl_2 \cdot$ (15-crown-5) $\cdot 3H_2O$ | 19.52 | 4.27 | 11.52 | 19.50 | 4.38 | 11.51 |
| $UO_2Cl_2 \cdot$ (12-crown-4) $\cdot 2H_2O$ | 17.37 | 3.65 | 12.82 | 17.38 | 3.20 | 12.86 |
| $(UO_2Cl_2)_2 \cdot$ (18-crown-6) | 15.23 | 2.56 | 14.99 | 15.57 | 2.69 | 14.96 |
| $(UO_2Cl_2)_2 \cdot$ (15-crown-5)$_3 \cdot$ 2HCl | 25.45 | 4.42 | 15.02 | 25.42 | 4.47 | 15.34 |
| $UO_2Cl_2 \cdot$ (12-crown-4) | 18.58 | 3.12 | 13.71 | 18.90 | 3.38 | 15.95 |
| $(UO_2Cl_2)_2 \cdot$ (dicyclohexano-18-crown-6) | 22.78 | 3.45 | 13.45 | 23.30 | 3.42 | 13.39 |

Infrared spectra of the complexes revealed that the C—O—C stretching vibration band, generally at about 1100 cm$^{-1}$, was lowered about 20–25 cm$^{-1}$ compared to the corresponding uncomplexed crown ether. Such a shift is indicative of coordination between the polyether and the metal ion.

The formation of complexes between uranyl halides and 18-crown-6 in accordance with this invention provides a technique for the selective separation of uranyl halides from other metal halides, i.e., nickel halide and cooper halide. This separation technique is based upon the discovery that when uranyl halide, nickel halide, and copper halide are dissolved in a liquid in which a uranyl halide crown ether complex can be formed, the uranyl halide crown ether complex is formed in preference to crown ether complexes with the copper and nickel halides. This preferential formation of the uranyl halide crown ether complex is illustrated by the following example:

EXAMPLE VIII

To 5 ml of a methanol solution containing 0.50 gm $NiCl_2 \cdot 6H_2O$, 0.36 gm $CuCl_2 \cdot 2H_2O$, and 0.83 gm $UO_2Cl_2 \cdot 3H_2O$ (i.e., 0.0021 mole of each) was added 0.0021 mole of 18-crown-6 in 5 ml of ethanol solution. Then 10 ml of diethyl ether was added to assist in precipitation of complexes. After 15 minutes of stirring, the sample was cooled in an ice bath; the precipitate was isolated, washed with more diethyl ether, and dried in vacuo. The precipitate weighed 1.0 gm and elemental analysis showed that it contained 67, 1, and 2.6 weight percent, respectively, of the original uranium, copper, and nickel.

In order to assure that the thus-observed phenomenon was due to the addition of the crown compound, another 5 ml portion of the methanol salt solution was treated identically except that the 5 ml portion of methanol which was admixed with the salt solution did not contain any crown ether. No precipitate formed. Accordingly, the previously observed precipitation can be attributed to the 18-crown-6.

Similar tests were made in which 15-crown-5 or 24-crown-8 were employed rather than 18-crown-6. Instead of showing good selectivity to precipitate uranium, these latter two cyclic polyethers exhibited greatest affinity for nickel. The actual numerical values from these tests are:

| | Percent Metal Precipitated | | |
|---|---|---|---|
| | U | Cu | Ni |
| 15-crown-5 | 10.0 | 7.5 | 32.5 |
| 24-crown-8 | 20.0 | 15.0 | 32.5 |

In accordance with another aspect of the invention 18-crown-6 is employed for the selective recovery of uranyl halide from a solution containing nickel halides and/or copper halides as well as uranyl halides. In using 18-crown-6 for the selective recovery of uranyl halides from a solution containing as well nickel and/or copper halides, the quantity of 18-crown-6 should not be substantially greater than that needed to complex with all the uranyl halide in the solution as this would result in the precipitate including additional copper and nickel. As indicated above, the amount of uranyl halide in the crown ether complex can vary depending upon whether or not a hydrated complex is formed. Accordingly, the maximum preferred amount of 18-crown-6 employed will depend upon the type of complex formed. In any case, a molar ratio of 18-crown-6 to uranyl halide of no more than 1 is quite suitable.

The uranyl halide crown ether complexes of this invention can be readily converted to a precipitate of uranium oxide hydrate by adding the complex to water containing carboxylate ion and exposing the mixture to light under suitable conditions.

Also uranium oxide hydrate can in accordance with the present invention be readily produced from aqueous solutions containing uranyl halides. In a preferred embodiment of this invention an aqueous solution containing uranyl halide is first extracted with an organic solvent for the uranyl salt which will permit the uranyl salt to form a recoverable complex with at least one of the above-specified crown ether compounds. Then to that organic solution of uranyl halide is added an amount of such crown ether sufficient to produce a solid containing at least one type of crown ether/uranyl halide complex. The crown ether/uranyl halide-containing solid is then contacted with water, carboxylate ion, and light under conditions sufficient to produce uranium oxide hydrate. The uranium oxide hydrate can be recovered from the water by conventional recovery techniques such as centrifugation or filtration. The recovered uranium oxide hydrate can then be dehydrated or converted to other desired forms by conventional processes.

By first extracting the aqueous uranyl salt solution with organic solvent for the uranyl halide salt, one obtains at least a partial separation of the uranyl halides from other metal salts in the aqueous solution that would tend to contaminate the desired uranium oxide product. The subsequent formation of at least one uranyl halide crown ether complex provides a further purification since the solid obtained will include primarily only those compounds that form complexes with such crown ether.

In an especially preferred embodiment of the present invention 18-crown-6 is employed in the forming of the complex that is converted to uranium oxide by the photochemical reaction. That embodiment is especially preferred because, as pointed out above, 18-crown-6 forms complexes with uranyl halides in preference to other metal halides. Thus 18-crown-6 provides even greater purification of the material which is to be exposed to the photochemical reaction.

The organic solvent suitable for extracting the uranyl halide from aqueous solutions thereof includes any organic liquids which are sufficiently insoluble in water to form a separate phase when mixed therewith, which have some solvent effect on the uranyl halide, and which do not cause dissociation of the crown ether complex. Examples of such liquids include 1-pentanol, diethyl ether, and tetrahydrofuran.

The carboxylate ion employed in the photochemical reaction can be provided by employing a carboxylic acid or a salt thereof. Carboxylic acids containing from 1 to 6 carbon atoms per molecule, such as formic acid, acetic acid, propionic acid, butyric acid, valeric acid, and caproic acid, and alkali metal or ammonium salts thereof are generally suitable. While the amount of carboxylate ion employed can vary over a wide range, for maximum production of uranium oxide hydrate, at least one equivalent of carboxylate ion should be employed for each equivalent of uranyl halide in the organic liquid. Preferably the reactant solution contains about 1 to about 10 moles of carboxylate ion per mole of uranyl halide.

The amount of water used in the photochemical reaction can vary over a wide range. Generally water is employed in such an amount that the uranium in said uranyl halide amounts to about 0.005 to about 10 weight percent of the weight of the water.

The photochemical reaction is believed to be caused by light having wavelength within the visible range of the spectrum. The preferred wavelength can be determined by routine experimentation. It is also within the scope of this invention to employ light having wavelengths in the infrared and/or ultraviolet ranges as well as light in the visible range, for example, sunlight can be employed.

For the irradiation process, any conditions can be employed which give the desired degree of uranium oxide production. The time for the reaction is highly dependent upon the intensity of the light source and the desired conversion of uranyl halide. Generally, the reaction time is within the range of about 10 seconds to about 24 hours, preferably in the range of about 1 minute to about 10 hours.

The temperature at which the irradiation is conducted is not considered to be critical. Of course, it is preferred that the temperature be such that a substantial amount of the uranyl salt will be in solution in the water. Generally then the temperature will be in the range of from greater than 0° C. to less than 100° C. and preferably 20° C. to 40° C.

The product of the irradiation will form as a precipitate comprising uranium oxide hydrate. That precipitate can be recovered by any well-known means in the art. For example, the precipitate can be recovered from the liquid by simple filtration. The recovered precipitate can then be used either directly or further purified and dried for use in well-known processes of producing uranium compounds.

Following the removal of the uranium oxide precipitate, the resulting solution can be treated to recover the remaining crown ether or carboxylate by well-known methods such as fractional distillation or solvent extraction. It is likewise within the scope of this invention to employ the recovered solution directly in dissolving more solid uranium-containing compounds for subsequent irradiation to recover more uranium oxide. It is likewise within the scope of this invention to evaporate water or alcohol from the recovered solution to obtain a concentrate of crown ether, carboxylate and solvent for subsequent addition to a uranium-containing solution followed by irradiation thereof.

From the foregoing description, one skilled in the art can easily ascertain the essential characteristics of this invention, and without departing from the spirit and scope thereof, make various changes and modifications to adapt the invention to various usages and conditions. Consequently, such changes and modifications are properly, equitably, and are intended to be within the scope of the following claims.

What is claimed is:

1. A complex of:
   (A) a uranyl halide; and
   (B) a crown ether selected from the group consisting of dicyclohexano-18-crown-6 and crown ethers wherein the cyclic ring consists of 4 to 10-O-J-units wherein J for a particular compound is (a) —CHR—CHR— or (b) —CHR—CR$_2$—CHR—, wherein each R is independently selected from the group consisting of hydrogen and alkyl radicals having from 1 to 4 carbon atoms, or wherein at least one J is (b) and the remaining J's are (a).

2. A complex according to claim 1 wherein the crown ether is one in which the cyclic ring contains no more than 24 atoms and in which the R's if alkyl have no more than two carbon atoms.

3. A complex according to claim 2 wherein the uranyl halide is hydrated.

4. A complex according to claim 2 having the formula $$UO_2Cl_2.(18\text{-crown-}6).3H_2O.$$

5. A complex according to claim 2 having the formula $$UO_2Cl_2.(15\text{-crown-}5).3H_2O.$$

6. A complex according to claim 2 having the formula $$UO_2Cl_2.(12\text{-crown-}4).2H_2O.$$

7. A complex according to claim 2 having the formula $$(UO_2Cl_2)_2.(18\text{-crown-}6).$$

8. A complex according to claim 2 having the formula $$(UO_2Cl_2)_2.(15\text{-crown-}5)_3.2HCl.$$

9. A uranyl halide complex according to claim 2 having the formula $$UO_2Cl_2.(12\text{-crown-}4).$$

10. A uranyl halide complex according to claim 2 having the formula $$(UO_2Cl_2)_2.(\text{dicyclohexano-18-crown-}6).$$

11. A method for producing a uranyl halide crown ether complex comprising admixing in a suitable liquid a uranyl halide with a crown ether selected from the group consisting of dicyclohexano-18-crown-6 and crown ethers wherein the cyclic ring consists of 4 to 10-O-J-units wherein J for a particular compound is

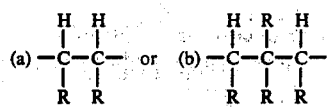

wherein each R is independently selected from the group consisting of hydrogen and alkyl radicals having from 1 to 4 carbon atoms, or wherein at least one J is (b) and the remaining J's are (a); and recovering the uranyl halide crown ether complex.

12. A method according to claim 11 wherein the crown ether is one in which the cyclic ring contains no more than 24 atoms and in which each R if alkyl has no more than two carbon atoms.

13. A method according to claim 12 wherein said admixing is conducted at a temperature in the range of about 20° to about 40° C.

14. A method according to claim 13 wherein said uranyl halide is selected from the group consisting of uranyl chloride, uranyl bromide, and uranyl iodide.

15. A method according to claim 14 wherein the uranyl halide has water associated therewith.

16. A method according to claim 15 wherein said crown ether is selected from the group consisting of 12-crown-4, 15-crown-5, 18-crown-6, and dicyclohexano-18-crown-6.

17. A method according to claim 16 wherein said uranyl halide and said crown ether are admixed in glacial acetic acid containing no more than 1 weight percent water.

18. A method according to claim 17 wherein the molar ratio of uranyl halide to crown ether is in the range of about 0.1:1 to about 10:1.

19. A method according to claim 18 wherein the weight ratio of glacial acetic acid to the combined weight of uranyl halide and crown ether is in the range of about 3:1 to about 20:1.

20. A method according to claim 19 wherein said uranyl halide is uranyl chloride trihydrate.

21. A method according to claim 20 wherein a solution of uranyl chloride trihydrate in glacial acetic acid is added to a solution of said crown ether in glacial acetic acid and said combined solutions are stirred until said uranyl chloride crown ether complex is formed.

22. A method according to claim 13 wherein said uranyl halide is anhydrous and said uranyl halide and said crown ether are admixed in an anhydrous liquid.

23. A method according to claim 22 wherein said anhydrous uranyl halide is selected from the group consisting of uranyl chloride, uranyl bromide, and uranyl iodide.

24. A method according to claim 23 wherein said uranyl halide and said crown ether are admixed in anhydrous acetic acid.

25. A method according to claim 24 wherein said crown ether is selected from the group consisting of 12-crown-4, 15-crown-5, 18-crown-6, and dicyclohexano-18-crown-6.

26. A method according to claim 25 wherein the molar ratio of said uranyl halide to said crown is in the range of about 0.1:1 to about 10:1.

27. A method according to claim 26 wherein said anhydrous acetic acid is a mixture of glacial acid and acetic anhydride.

28. A method according to claim 27 wherein said anhydrous acetic acid is a mixture of glacial acetic acid and about 5 to about 10 weight percent of acetic anhydride.

29. A method according to claim 28 wherein said uranyl halide is anhydrous uranyl chloride.

30. A method according to claim 11 wherein said uranyl halide is anhydrous and said uranyl halide and said crown ether are admixed in an anhydrous liquid.

31. A process for the selective separation of at least one uranyl halide from one or more nickel halides and/or copper halides comprising dissolving said at least one halide in a solvent in which a uranyl halide.-18-crown-6 complex is stable and admixing 18-crown-6 therewith under conditions such that a uranyl halide.18-crown-6 complex is formed, wherein said 18-crown-6 is in an amount no greater than the amount needed to complex all of the uranyl halide in the solution, and recovering the uranyl halide.-18-crown-6 complex that is formed.

32. A process according to claim 31 wherein the moles of 18-crown-6 employed are no greater than the number of moles of uranyl halide in the solution.

33. A process according to claim 31 wherein said at least one uranyl halide is dissolved in methanol and diethyl ether is added to precipitate the uranyl halide.18-crown-6 complex after said complex is formed.

34. A process for obtaining uranium oxide from an aqueous solution of uranyl halide comprising:
extracting uranyl halide from said aqueous solution with an organic solvent which will permit the formation of recoverable uranyl halide crown ether complex;
forming at least one uranyl halide crown ether complex by admixing with the organic solution of uranyl halide a suitable amount of at least one crown ether selected from the group consisting of dicyclohexyl-18-crown-6 and crown ethers wherein the cyclic ring consists of 4 to 10-O-J-units wherein J for a particular compound is

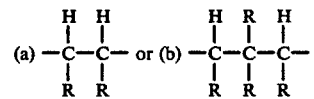

wherein each R is indpendently selected from the group consisting of hydrogen and alkyl radicals having from 1 to 4 carbon atoms, or wherein at least one J is (b) and the remaining J's are (a);
contacting said uranyl halide crown ether complex with water, carboxylate ion, and light under conditions sufficient to produce uranium oxide hydrate; and
recovering said uranium oxide hydrate.

35. A process according to claim 34 wherein said crown ether is selected from the crown containing no more than 24 atoms in the cyclic ring and in which each R if alkyl has no more than two carbon atoms.

36. A process according to claim 35 wherein said at least one crown ether is selected from the group consisting of dicyclohexano-18-crown-6, 12-crown-4, 15-crown-5, 18-crown-6, and 24-crown-8.

37. A process according to claim 36 wherein the water is employed in such an amount that the uranium in said uranyl halide amounts to about 0.005 to about 10 weight percent of the weight of the water.

38. A method according to claim 37 wherein about 1 to about 10 moles of carboxylate ion is employed per mole of uranyl halide.

39. A method according to claim 38 wherein said uranyl halide crown ether complex is converted to uranium at a temperature in the range of about 20° C. to about 40° C.

40. A method according to claim 29 wherein the sole crown ether complex employed is 18-crown-6.

41. A method according to claim 16 wherein said uranyl halide and said crown ether are admixed in diethyl ether.

42. A method according to claim 41 wherein said crown ether is 15-crown-5.

43. A method according to claim 42 wherein said uranyl halide is uranyl chloride trihydrate.

44. A method according to claim 13 wherein said uranyl halide is uranyl chloride.

45. A method according to claim 11 wherein said uranyl halide is anhydrous and said uranyl halide and said crown ether are admixed in an anhydrous liquid.

* * * * *

UNITED STATES PATENT AND TRADEMARK OFFICE
CERTIFICATE OF CORRECTION

PATENT NO. : 4,186,175

DATED : January 29, 1980

INVENTOR(S) : David L. Tomaja

It is certified that error appears in the above–identified patent and that said Letters Patent are hereby corrected as shown below:

Column 10, line 57, after "crown" second occurrence, insert --- ethers ---.

Column 11, line 11, delete "29" and substitute therefor --- 39 ---.

Signed and Sealed this

Sixth Day of May 1980

[SEAL]

Attest:

SIDNEY A. DIAMOND

Attesting Officer

Commissioner of Patents and Trademarks